United States Patent [19]
Hartman

[11] Patent Number: 5,623,561
[45] Date of Patent: Apr. 22, 1997

[54] INTEGRATED OPTIC INTERFEROMETRIC SENSOR

[75] Inventor: Nile F. Hartman, Stone Mountain, Ga.

[73] Assignee: Georgia Tech Research Corporation, Atlanta, Ga.

[21] Appl. No.: 535,569

[22] Filed: Sep. 29, 1995

[51] Int. Cl.$^6$ .................................................. G02B 6/00
[52] U.S. Cl. ................................................................. 385/12
[58] Field of Search ........................... 385/12–16, 30; 250/227.21; 372/102

[56] References Cited

U.S. PATENT DOCUMENTS

| | | | |
|---|---|---|---|
| 4,515,430 | 5/1985 | Johnson | 385/12 |
| 4,940,328 | 7/1990 | Hartman | 356/345 |
| 4,969,742 | 11/1990 | Falk et al. | 356/345 |
| 5,091,983 | 2/1992 | Lukosz | 385/13 |
| 5,120,131 | 6/1992 | Lukosz | 356/351 |
| 5,226,100 | 7/1993 | Maerz | 385/24 |
| 5,442,169 | 8/1995 | Kunz | 250/227.21 |
| 5,448,665 | 9/1995 | Kershaw et al. | 385/30 |
| 5,491,762 | 2/1996 | Deacon et al. | 385/16 |
| 5,504,772 | 4/1996 | Deacon et al. | 372/102 |

OTHER PUBLICATIONS

*Waveguide Grating for Polarization Preprocessing Circuits*, G. Voirin, F. Gradisnik, O. Parriaux, M.T. Gale, R.E. Kunz, B.J. Curtin, and H.W. Lehmann, SPIE vol. 1126 Electro–Optic and Magneto–Optic Materials and Applications (1989).
*Totally Integrated Optical Measuring Sensors*, R. E. Kunz, SPI vol. 1587 Chemical, Biochemical and Environmental Fiber Sensors III (1991).
*Integrated Optical Approaches to Signal and Data Processing*, C.M. Verber and R.P. Kenan, presented at National Aerospace and Electronics Conference NAECON 84, Dayton Conventional Center, Dayton, Ohio, May 21–25, 1984.

Primary Examiner—Akm E. Ullah
Attorney, Agent, or Firm—Needle & Rosenberg, P.C.

[57] ABSTRACT

An improved integrated optic interferometric sensor uses a planar waveguide to offer detection sensitivity equal to the Mach-Zehnder interferometric sensor, while retaining the input coupling and manufacturing ease characteristic of a planar waveguide. Enhanced output signal processing capabilities are provided by use of at least two integrated optic interferometric sensors employing planar constructs.

44 Claims, 10 Drawing Sheets

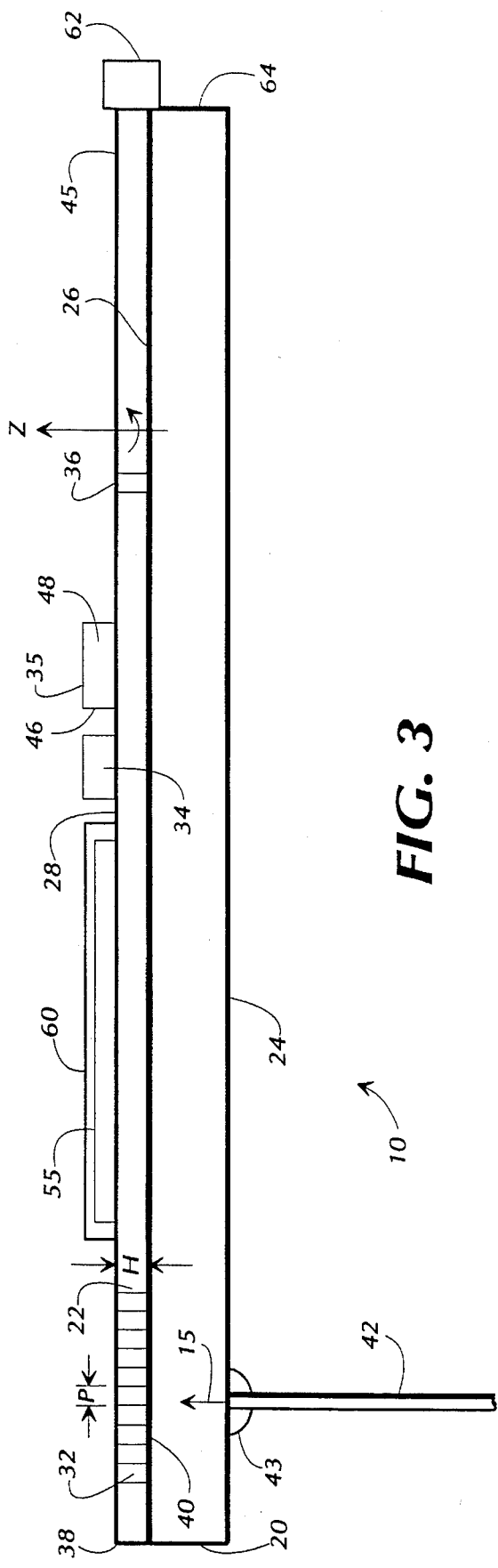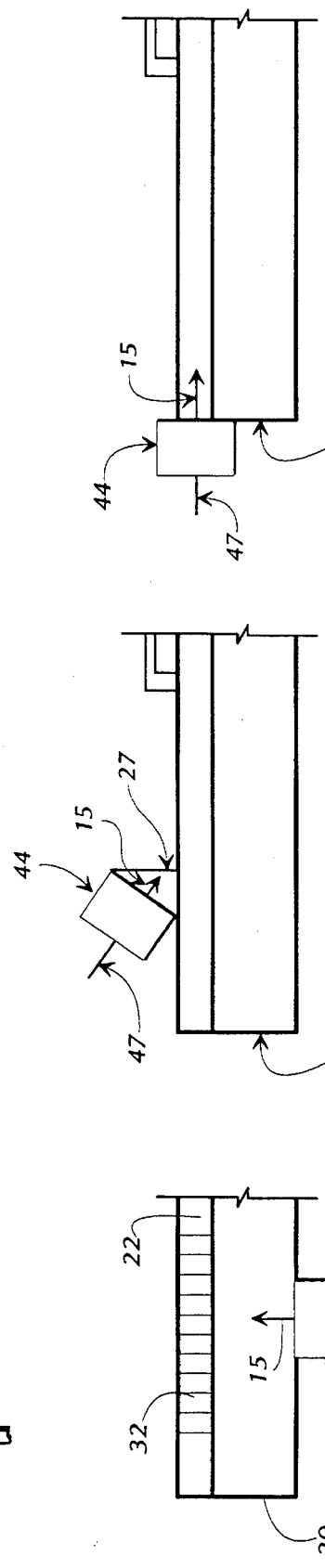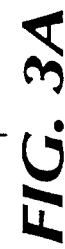
FIG. 3
FIG. 3A
FIG. 3B
FIG. 3C

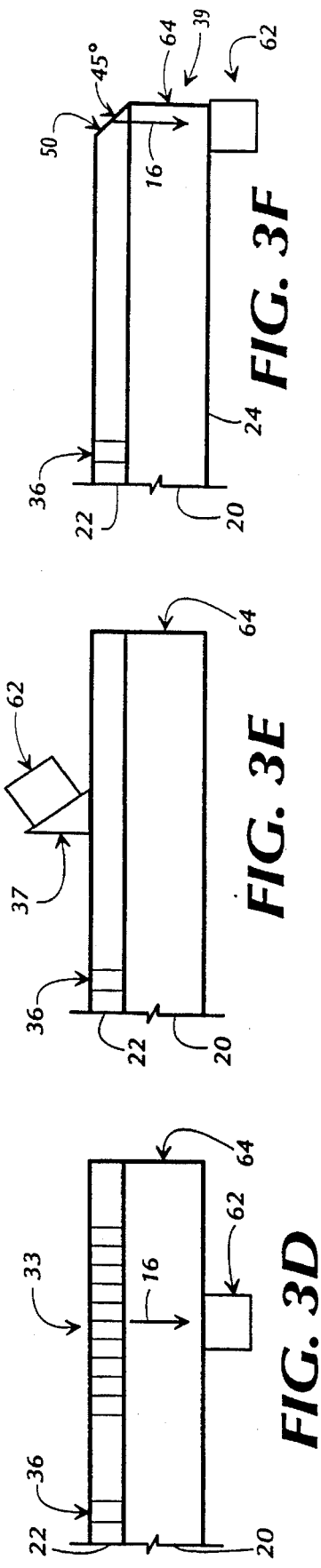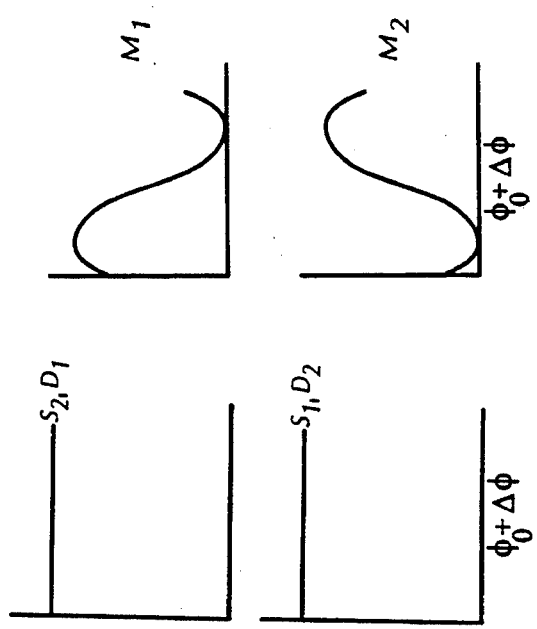

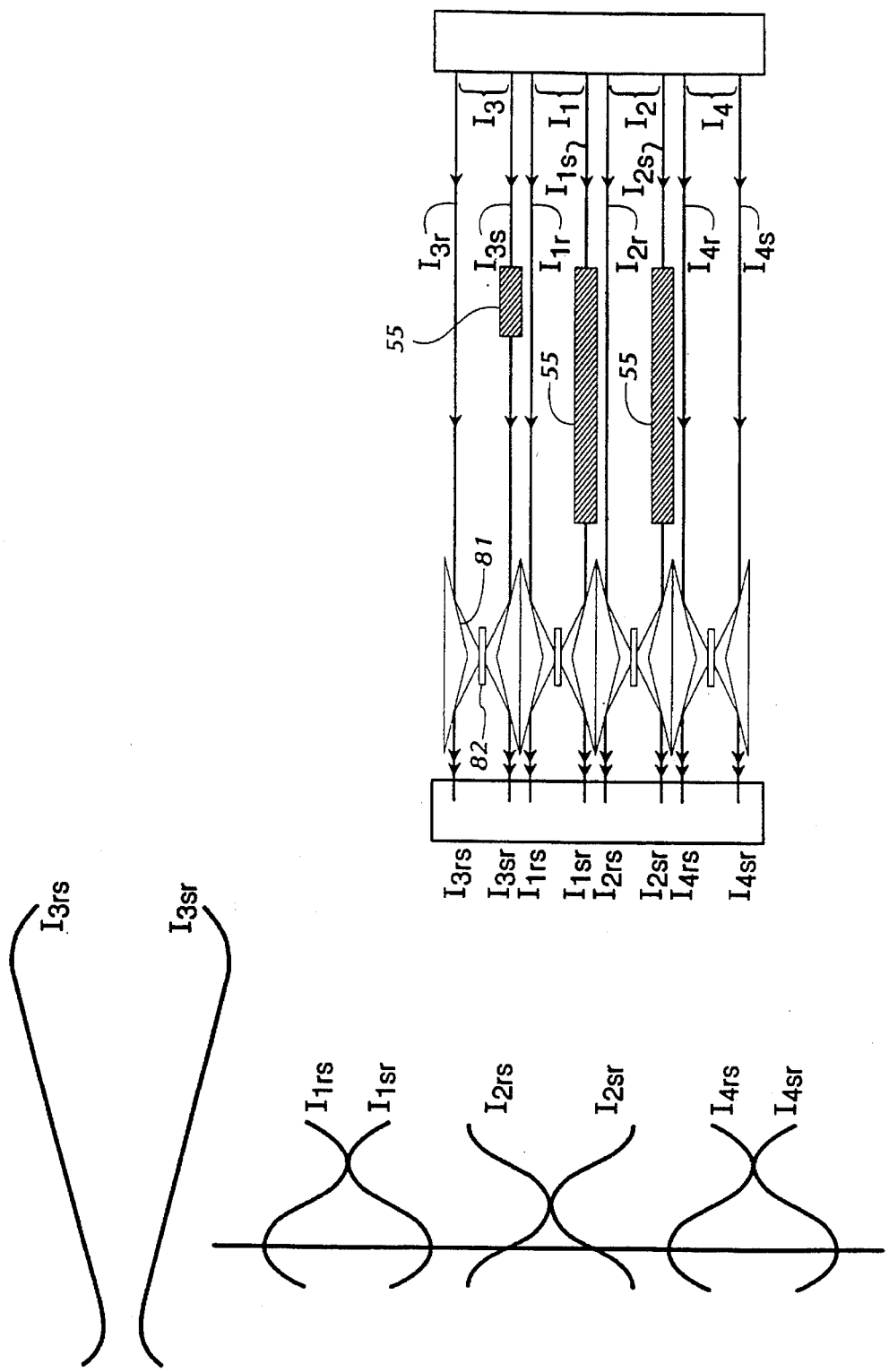

INTEGRATED OPTIC INTERFEROMETRIC SENSOR

FIELD OF THE INVENTION

The present invention relates to a sensor and more particularly to an optic interferometric sensor for measuring properties of an environment to which it is exposed.

BACKGROUND OF THE INVENTION

Sensors for detecting and measuring absolute or relative values of physical quantities such as chemical or biochemical concentration, magnetic or electric field strengths, pressure, strain, temperature, and pH, for example, in an environment to which the sensor is exposed, are well known in the art. Prior art sensors include direct reading sensors, which include, for example, a mercury thermometer or Bourdon pressure gauge, and sensors that employ transducers for converting an input signal or stimulus into an output signal of a different type. Thus, an infrared pyrometer converts infrared radiation into a useful electrical output signal readable by an electrical meter.

Prior art sensors also include optic sensors which provide measured values directly or by means of transducers. A simple color comparison pH test apparatus is an example of optic sensor read directly whereas a camera light intensity metering system is optic sensor employing a transducer. The most sensitive optic sensor is of the interferometric type, which employs an interferometer to provide information about a condition sensed. An interferometer is an instrument that splits light from an input source into two or more light beams. The light beams are caused to travel through different paths with different effective optical path lengths so that an interference fringe pattern is produced when the beams are recombined. An analysis of the light and dark bands of the interference pattern provides a sensitive measure of the difference in effective path length of the different optical paths.

A particular group of optic sensors which has experienced significant technical development in recent years includes integrated optic sensors. Integrated optic sensors are monolithic structures characterized by the integration of various optical components into a single optic waveguide construction. An integrated optic sensor is typically a thin-film device comprising a waveguide constructed on a single substrate, which generally provides other optical elements or components to diffract, refract, reflect, or combine different beam portions propagating in the waveguide. Integrated optic technology is particularly useful in providing the optical elements heretofore associated with interferometric sensors employing separate and discrete optical components. The prior art now includes integrated optic sensors that incorporate a variety of components including lenses, sensing fields, and filters on a single substrate.

A typical integrated optic sensor comprises one or more channel waveguides fabricated as a planar construct on a substrate. A channel waveguide is a linear structure of typically small cross-section, on the order of several micrometers wide by several micrometers high, providing an optical path for a propagating light beam. The index of refraction of the channel waveguide is higher than the index of refraction of the surrounding or supporting substrate. A light source and possibly a coupling mechanism are provided to cause a light beam to propagate within the channel waveguide. The light source can be a laser, a light emitting diode (LED), or an incandescent light source. The propagating light beam passes through a sensing region of the channel waveguide which is reactive to particular conditions of the environment. The environment may cause changes in the propagation characteristics of the channel waveguide, such as a change in the refractive index. The change in the refractive index changes the effective path length through the channel region, thereby changing the phase of the light beam as it emerges from the channel waveguide. Alternatively, if the channel waveguide is not directly sensitive to a particular environment, it may be coated with a material that is reactive to the environment, or to a component thereof, causing a change in the refractive index of the channel waveguide. An optical output beam from the sensor can therefore be used for measuring the relative or absolute value of the condition of the environment.

The optical input beam propagates through the waveguide in modes which satisfy the well-known Maxwell equations. Maxwell equations govern the electric and magnetic fields of an electromagnetic wave propagating through a medium. The modes may be characterized by the frequency, polarization, transverse field distribution and phase velocity of the constituent waves. In rectangular channel waveguides the modes are designated as $TE_{m,n}$ and $TM_{m,n}$ which are orthogonally polarized components of the light beam, transverse electric and transverse magnetic, respectively, with mode number indices m and n taking non-negative integer values. Each mode represents a different field distribution corresponding to the number of wave nodes across the waveguide in each direction. The allowed modes are determined by the configuration of the boundaries of the waveguide, which for integrated optic sensors are the interfaces between the substrate and waveguide, the environment and the waveguide, and/or the coating and the waveguide. Depending on the boundaries and the wavelength of the input light source, no modes, one mode, or more than one mode may be allowed to propagate through the waveguide.

Commercially available integrated optic interferometers include those utilizing a Mach-Zehnder interferometric technique, such as that disclosed in U.S. Pat. No. 4,515,430, which is incorporated herein by reference. This technique is characterized by single mode propagation of two light beams through two light paths, then combining the two beams to produce an optical interference pattern. Generally, a Mach-Zehnder device receives a single input light beam which is then split by a beam splitter into two beams that are directed through two different channel waveguides. Changes in the optical path length of one of the waveguides are effected when the environment causes a change in its physical length or a change in its refractive index. The beams emerging from the channel waveguides are recombined to produce a single interfering beam which is indicative of the relative or absolute change caused by exposing the device to the environment.

Integrated optic interferometers employing the Mach-Zehnder configuration provide outstanding sensitivity and can be made in small sizes. These sensors, however, suffer in that they rely on two or more single-mode channel waveguides with typical cross-sectional dimensions of 2 μm by 3 μm each, making fabrication difficult and costly. Furthermore, the two channel waveguides can be affected differently by thermal and vibration aspects of the environment, leading to spurious interference effects. Most importantly, the small size of the channels make efficient light coupling difficult to achieve with Mach-Zehnder interferometers. The light coupling difficulty makes this type of interferometer all but useless for many applications.

A second type of integrated optic interferometric sensor uses a planar waveguide as the planar construct. A planar waveguide is defined by only two (parallel) boundaries, rather than the four rectangular boundaries typical of a channel waveguide. In a planar waveguide, the propagating modes are designated as $TE_m$ and $TM_m$ (transverse electric and transverse magnetic, respectively), with the mode number index m taking non-negative integer values. As in the channel waveguide, the boundaries and the wavelength of the input light source determine whether no modes, one mode, or more than one mode may be allowed to propagate through the waveguide.

In the descriptions of the prior art and of the invention in this specification, the terms "planar construct" and "planar waveguide" refer to structures that are generally planar in their overall construction. However, it should be understood that planar constructs and planar waveguides can incorporate such features as grooved or ridged surfaces, porous layers or regions, or other embedded or surface relief features. In addition, the descriptions herein of the prior art and of the invention use the term "optic" and "light," but it must be recognized that the techniques described are phenomena of electromagnetic radiation in general. Thus, the term "optic" and "light" herein should be read as referring to any electromagnetic radiation that meets whatever constraints are imposed by the characteristics of the various components of the sensor (such as the dimensions of the optical path) and the nature of the interaction between the sensor and properties of the environment to be sensed (such as the sensitivity of the sensor as a function of wavelength). Typically, the light will be in the visible or near-visible wavelength range.

Planar waveguide interferometric sensors are disclosed in U.S. Pat. No. 4,940,328, issued to Hartman, and U.S. Pat. No. 5,120,131, issued to Lukosz, which patents are incorporated herein by reference. In the devices described in these patents, light is propagated in at least two modes in a single planar waveguide, as opposed to propagating in multiple channel waveguides, and passes through a sensing field exposed to the environment to be measured. The sensor output includes a beam comprising the interference products of at least two of the modes propagating in the planar waveguide. The higher order modes are most influenced when the environment causes a change in the refractive index of the planar waveguide and, when combined with the lower order modes, provide an output showing intermodal interference. These devices are more easily fabricated than the single mode Mach-Zehnder devices and are characterized by easier light coupling into the waveguide. However, the sensitivity of these devices is generally only one-half to one-third the sensitivity of the Mach-Zehnder devices. The lower sensitivity is the result of the fact that the lower order mode is not completely unaffected by the environmental stimulus and it therefore does not provide a true reference beam.

Another problem with the prior art devices is their inability to achieve high levels of integration of optical components in a single waveguide utilizing a single processing technology.

The above deficiencies greatly reduce the usefulness of integrated optic sensors and increase their cost. What is needed and what is not currently available is an integrated optic sensor that is relatively inexpensive, incorporates a high degree of component integration into a single waveguide, and provides high sensitivity with simple and efficient light coupling.

SUMMARY OF THE INVENTION

The foregoing problems of the prior art have been overcome by the integrated optic interferometric sensor of this invention. When provided with a light beam from a light source, the sensor provides an output signal indicative of a property or condition of the environment to which the sensor is exposed.

In one embodiment, the sensor is comprised of a planar waveguide, an integrated optic diffraction grating, an integrated optic biprism, and a phase grating. The diffraction grating injects, or couples, a light beam from the light source into the planar waveguide such that only one mode of the light beam propagates in the planar waveguide. In the waveguide, a first portion of the light beam is affected in a first manner by the property of the environment, and a second portion of the light beam is affected in a second manner by the property the environment. The first portion of the light beam is in a first region of the waveguide, separated spatially from the second portion of the light beam in a second region of the waveguide The integrated optic biprism deflects the beam portions so that the first beam portion intersects the second beam portion. The phase grating is placed at the point of intersection of the beam portions so as to produce at least one output beam indicative of at least one combination of the beam portions.

Alternate embodiments may be provided by replacing the diffraction grating with other light input couplers, such as prisms, mirrors or by suitably mounting the light source so as to eliminate the need for the light input coupler. Similarly, the integrated optic biprism, serving as a beam deflector, may be replaced by an integrated optic lens, an integrated optic diffraction grating, or a total internal reflection element. In addition, the phase grating, serving as a beam combiner, may be replaced by a Fresnel reflection element, an acousto-optic device, or an electro-optic device.

A portion of the planar waveguide of the sensor may be treated to enhance the effect that the property of the environment has on the first portion of the light beam in the waveguide. The treatment may consist of coating the portion of the planar waveguide with a material whose refractive index varies in response to any variance of the property of the environment. Alternatively, the treatment may consist of coating the portion of the planar waveguide with a material whose thickness varies in response to any variance of the property of the environment, or coating the portion of the planar waveguide with a material which reacts with a substance in the environment. The treatment may also minimize, rather than enhance, the effect the property of the environment has on either the first or the second portion of said light beam. Rather than treating the waveguide, at least a portion of the planar waveguide itself may be constructed from a material whose refractive index varies in response to any variance of the property of the environment, or whose configuration (e.g., shape or size) varies in response to any variance of the property of the environment, or from a material which interacts with a substance in the environment.

Preferably, the planar waveguide is fabricated on a substrate chosen for mechanical strength, toughness, or optical properties. Generally, the substrate, if present, underlies the entire sensor and provides a base for fabrication of the other sensor elements. In this specification, the term "waveguide structure" includes the planar waveguide itself in addition to any substrate which may be present and any coating which may be applied to the planar waveguide.

A distinguishing feature of the invention is that it is not necessary for the first and second regions of the planar waveguide to be separated into distinct "channel waveguides" by any longitudinal structure or interface, as is typical for Mach-Zehnder interferometers. The first and second regions comprise a beam processing region of the invention, which is defined only by upper and lower surfaces; there are no vertical, longitudinal interfaces (side boundaries) between the first and second regions. With respect to this structural feature, the present invention is like the device described by prior U.S. Pat. No. 4,940,328, but the present invention employs only a single transverse mode propagating in the planar waveguide, thereby increasing the sensitivity over the multimode device of U.S. Pat. No. 4,940,328 by a factor of two to three. With the added signal processing capabilities disclosed in this specification, the signal-to-noise ratio increases by more than an order of magnitude over the multimode device of U.S. Pat. No. 4,940,328.

The environment to which the sensor is exposed may directly affect the propagation of light through at least one sensing region of the planar waveguide by causing a change in the refractive index of that region. A change in the propagation of light through the affected region of the planar waveguide provides information regarding the environmental condition sensed. As indicated above, an external coating may be applied to at least one sensing region of the waveguide, if the environment is not directly able to alter the propagation of light through the waveguide. The coating is reactive to the environmental condition and affects the propagation of light through the waveguide.

One or more photodetectors may be provided to detect the output beam. The photodetector may be mounted to receive the output beam directly, fabricated integrally with the sensor, or various light output couplers, such as diffraction gratings, prisms, or mirrors may be employed to couple the outputs from the sensor to the photodetectors. Processing of the photodetector signals may be enhanced by constructing multiple integrated optic sensing regions (i.e., multiple interferometers) of different configurations (e.g., lengths, thicknesses, shapes, etc.) or of different materials (i.e., such as those having different optical or chemical properties, etc.).

The present invention provides at least two major signal processing enhancements by the use of multiple interferometers. The signal processing enhancements are applicable to planar construct interferometric sensors having channel waveguides (such as Mach-Zehnder devices) as well as those having planar waveguides, and are applicable regardless of the number or type of modes propagating in the planar construct. In the first of the two enhancements, a constant phase bias difference between the interferometer output beams is enabled by varying the construction parameters of the sensor, such as the planar construct configuration, the planar construct materials, the overlay configuration, the overlay materials, the substrate configuration, or the substrate materials. In particular, a constant phase bias difference of approximately ninety degrees ensures that maximum sensitivity is always available from the sensor. With other variations in the same construction parameters, the second of the two enhancements is enabled. This enhancement causes the output interference pattern of an output beam associated with one of interferometers to have a different slope at quadrature compared to the output interference pattern from the other interferometer. The different slopes ensure that both high resolution information and low resolution information are available from the same sensor.

In this specification, one of the waveguide sensing regions is called the "reference region." Any other waveguide sensing region, the propagation of light through which is affected by factors in the environment, is called a "signal region." For convenience, the "reference region" is typically the region where light propagation is unaffected or affected the least by factors in the environment, as compared with the signal regions.

In a preferred embodiment of the present invention the sensing regions are disposed in a common waveguide structure which is small in size. Because of this, environmental thermal and mechanical conditions tend to affect the entire sensor uniformly. Thus, there is no need for mechanical construction, necessary with other sensor types and configurations, to provide for temperature or vibration stability.

It is preferable that fabrication of the integrated optic components be accomplished by utilizing a single fabrication technology or a series of compatible technologies so that several integrated optic components may be formed in the sensor in a single manufacturing process. Thus, the selection of materials and fabrication techniques is important to the economic viability of these sensor devices. Current fabrication techniques include thin film deposition, ion exchange, ion implantation and vapor deposition which utilize photolithography and holographic etching processing. Gratings, for example, can be formed using twin beam interference patterns to create grating etch masks. The etch masks are removed after etching leaving the desired surface topology for the integrated optic grating.

Thus, it is an object of the present invention to provide an improved integrated optic interferometric sensor.

It is a further object of the present invention to provide an optical sensor having enhanced thermal and mechanical stability so that reliable measurements may be obtained under a variety of environmental conditions.

It is still a further object of the present invention to provide an integrated optic interferometer which has a high sensor sensitivity, which couples easily with an input light source, and which may be fabricated at low cost.

It is a further object of the present invention to provide a sensor sensitive to a variety of environmental conditions including temperature, humidity, and chemical and biochemical composition, for example.

If is a further object of the present invention to provide enhanced optical beam manipulation and signal processing capabilities.

It is a further object of the present invention to provide a high level of integration of optical components in a single device to improve stability and signal-to-noise ratios and so that a single processing technology can be employed.

Other objects and features of the present invention will be more readily understood from the following detailed description of specific embodiments thereof when read in conjunction with the accompanying drawings.

BRIEF DESCRIPTION OF THE DRAWINGS

FIG. 3 is a cross-sectional view of the embodiment shown in FIG. 1, taken along lines 3—3 of FIG. 1, showing a side view of the integrated optic elements of the interferometric sensor.

FIG. 3A is a partial cross-sectional view of an embodiment similar to that shown in FIG. 1, taken along lines 3—3 of FIG. 1, showing the replacement of the fiber optic pigtail by a laser diode.

FIG. 3B is a partial cross-sectional view of an embodiment similar to that shown in FIG. 1, taken along lines 3—3 of FIG. 1, showing a prism as the light-input coupling means.

FIG. 3C is a partial cross-sectional view of an embodiment similar to that shown in FIG. 1, taken along lines 3—3 of FIG. 1, showing light input by direct butt-coupling.

FIG. 3D is a partial cross-sectional view of an embodiment similar to that shown in FIG. 1, taken along lines 3—3 of FIG. 1, showing a grating as the light-output coupling means.

FIG. 3E is a partial cross-sectional view of an embodiment similar to that shown in FIG. 1, taken along lines 3—3 of FIG. 1, showing a prism as the light-output coupling means.

FIG. 3F is a partial cross-sectional view of an embodiment similar to that shown in FIG. 1, taken along lines 3—3 of FIG. 1, showing light output by a total internal reflection mirror.

FIG. 4A is a graphical representation of the input pattern of the optical output beams of the sensor of the present invention showing the amplitude of the beam as a function of phase shift $\Delta F$.

FIG. 4B is a graphical representation of the sinusoidal output pattern of the optical output beams of the sensor of the present invention showing the amplitude of the beam as a function of phase shift $\Delta F$.

FIGS. 7A and 7B show a control interferometric sensor and three additional interferometric sensors in a common structure, the output interference patterns for two of the interferometric sensors having different lengths for the environmentally-sensitive selective overlay on the signal regions, thereby producing different sensitivities in the signals emanating from the two signal regions, and the output interference pattern for another of the interferometric sensors having a different configuration or material for the waveguide or substrate in the signal region, thereby producing a different constant phase bias in the signal emanating from the signal region.

DETAILED DESCRIPTION

Figure 1:
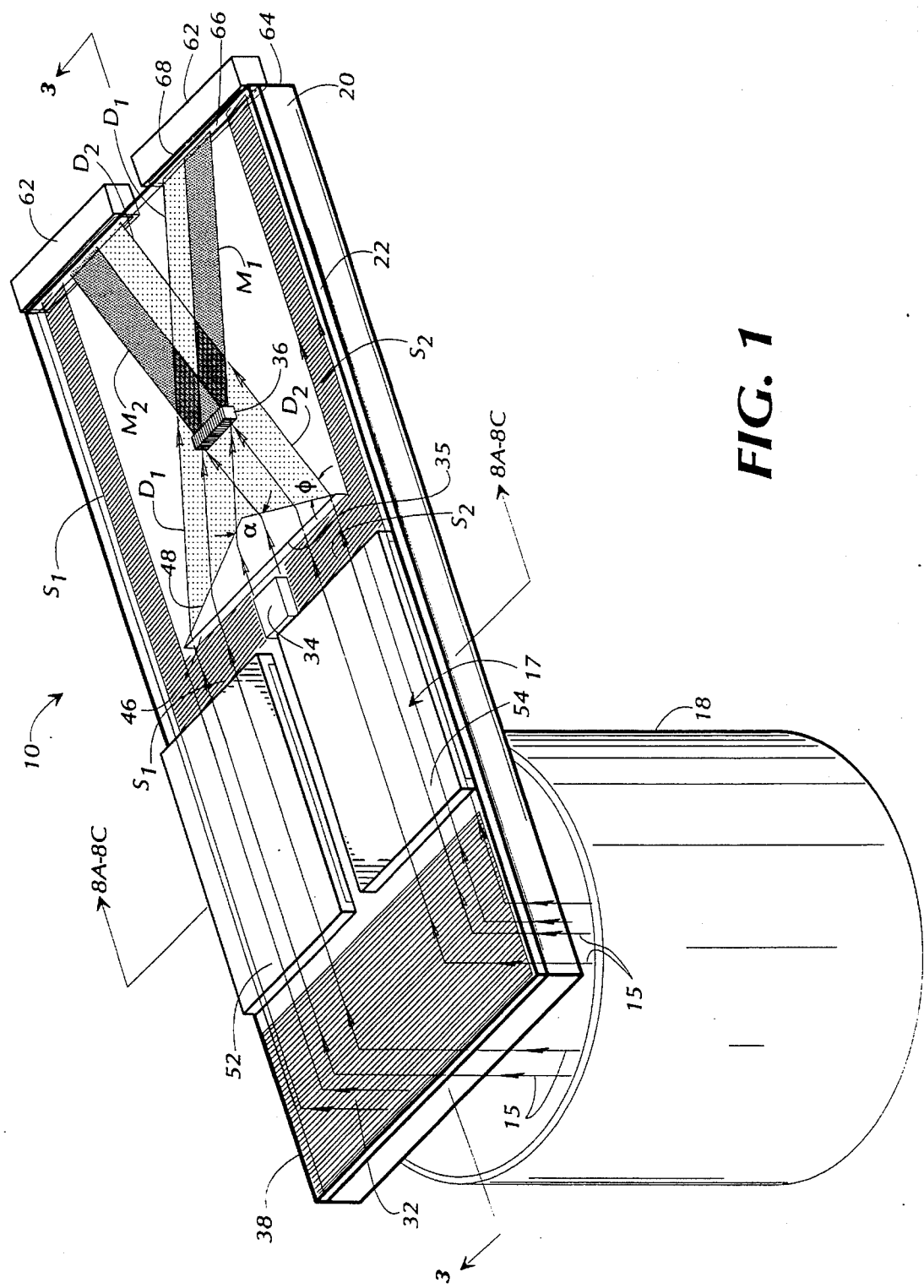
FIG. 1 is a perspective view of an embodiment of the interferometric sensor of the present invention.

Looking now at FIG. 1, there is shown a preferred embodiment of an integrated optic interferometric sensor for measuring a physical property of an environment to which the sensor is exposed, which is generally designated by the numeral 10. The sensor 10 is shown as being generally rectangular but it should be understood by those skilled in the art of integrated optics that other general configurations may be used depending on fabrication techniques, the final embodiment of the complete sensor system and other design and manufacturing preferences and considerations. The sensor 10 comprises a waveguide structure 12 (shown in FIGS. 8A–8C) through which a light beam is propagated and which contains integrated optic elements which, as will be more clearly explained below, manipulate the propagated optical beam in a desired manner. A light source 18 provides a light beam 15 to be propagated in the waveguide structure 12. Photodetector arrays 62 react to the output light beams of the waveguide and produce an electronic signal responsive to the detected light. An integrated optic beam processing region 17 provides the transducer capabilities of the sensor by causing the propagation of light through the waveguide structure 12 to be altered in response to an external environmental stimulus or condition which is desired to be measured or quantified. A protective covering (not shown) can be placed over all other regions of the sensor 10 to ensure that only the beam processing region 17 is exposed to the environment.

Figure 8A:
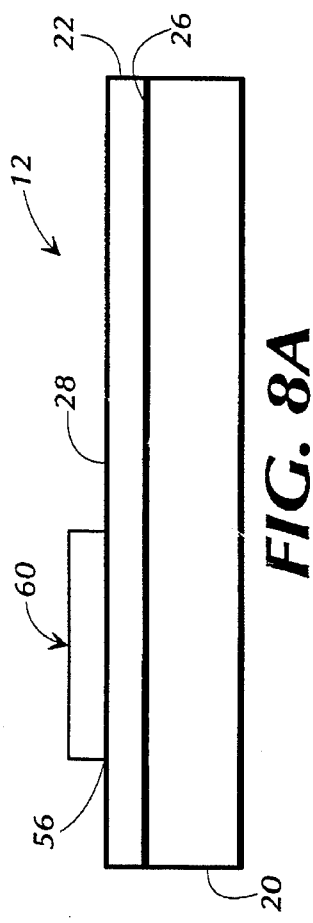
FIG. 8A is a cross-sectional view of the embodiment shown in FIG. 1, taken along lines 8A—8A of FIG. 1, showing in exaggerated fashion a single protective overlay defining a reference region.
Figure 8B:
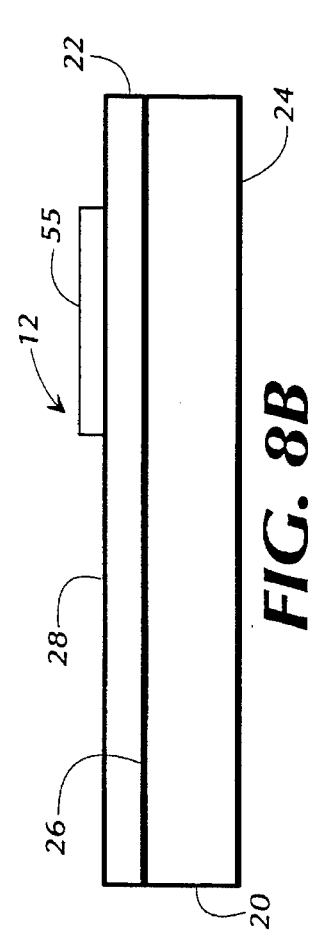
FIG. 8B is a cross-sectional view of an embodiment similar to that shown in FIG. 1, taken along lines 8B—8B of FIG. 1, showing in exaggerated fashion a single selective overlay defining a signal region.
Figure 8C:
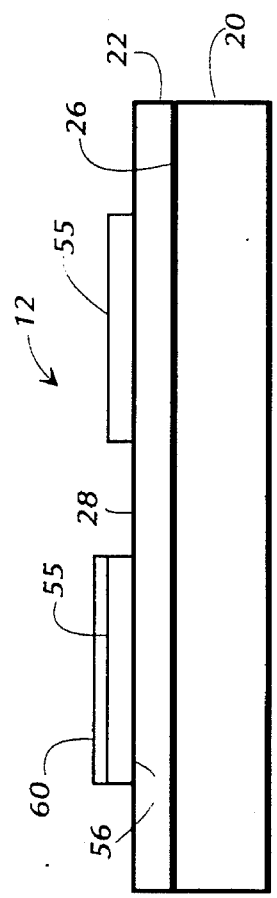
FIG. 8C is a cross-sectional view of an embodiment similar to that shown in FIG. 1, taken along lines 8C—8C of FIG. 1, showing in exaggerated fashion selective overlays defining a reference region and a signal region and wherein the reference region has also received a protective overlay.

The waveguide structure 12, which is shown in a series of cross-sections in FIGS. 8A–8C, includes a planar waveguide 22, and possibly a substrate 20, one or more selective overlays 55 and one or more protective overlays 60. The substrate 20 includes a substrate lower surface 24 and a substrate-waveguide interface surface 26. The substrate lower surface 24 and the substrate-waveguide interface surface 26 lie in substantially parallel planes. The planar waveguide 22 is a thin film of optically transmitting material having a waveguide upper surface 28 and a substrate-waveguide interface surface 26, the surfaces 28 and 26 also lying in substantially parallel planes. The substrate 20 also comprises an optically transmitting material.

The index of refraction of the waveguide 22 is greater than the refractive index of the substrate 20. The refractive index difference is effective to cause total internal reflection of light propagating through the waveguide 22 to prevent the light from leaving the waveguide 22. Although the light is totally internally reflected, electric and magnetic fields are induced in the region external to and close to the boundaries of the waveguide. These induced fields are called "evanescent fields."

Material selection for the waveguide structure 12 is application specific. The substrate 20 is often fabricated of compounds containing silica, including silicon dioxide doped with boron, for example. The waveguide 22 may be fabricated of glasses and other transparent dielectric materials including polymers. The glassy materials include, for example, silicon nitride or titanium doped silicon dioxide. The polymer materials include, for example, polyimides.

The materials chosen must be capable of providing a prescribed refractive index difference, $\Delta N$, between the substrate and waveguide material where the refractive index, N, of the waveguide is higher than that of the substrate. The refractive index of materials often used for optical interferometric sensor substrates falls in the general range of 1.4 to 1.6. The waveguide refractive index typically falls in the range of 1.4 to 4. In a preferred embodiment for an organic vapor detection sensor, the substrate material may be a BK7 type borosilicate glass with an N of 1.515 to which is applied a waveguide layer having a refractive index of 1.520, with a $\Delta N$ of 0.005.

The waveguide 22 may be either applied to the substrate 20 as a discrete layer of the waveguide structure or may be formed in the substrate 20. In the former case, the waveguide is applied to the substrate 20 by methods including chemical vapor deposition (CVD), thin film evaporation and vacuum sputtering. Where the waveguide 22 is formed in the substrate 20, methods including ion implantation and ion exchange may be used. Using either of these processes, the refractive index of the portion of the substrate adjacent to the waveguide upper surface 28 of the substrate 20 can be increased to a predetermined depth of 0.1 to 10 µm into the substrate 20 by changing the local chemical composition. Waveguide thicknesses of 0.1 to 10 µm are achievable by these processes. In the preferred embodiment for an organic vapor detection sensor the waveguide may be formed in a BK7 borosilicate substrate by the ion exchange process whereby silver ions are exchanged for sodium or potassium ions at the waveguide upper surface 28 of the substrate 20.

The integrated optic elements of the sensor 10 include an integrated optic light input coupling grating 32, an integrated optic light block 34, an integrated optic biprism 35 and an integrated optic phase grating 36. The input coupling grating 32 couples light into the planar waveguide 22 so that it will propagate within the waveguide along a desired path. The input coupling grating 32 and the integrated optic phase grating 36 may be gratings placed on or embedded in the surface of the planar waveguide 22. The propagating light beam is effectively bifurcated as it becomes incident on the light block 34 so as to define a pair of beams, one being a reference beam, $S_1$, and the other a signal beam, $S_2$. The light beams $S_1$ and $S_2$ are deflected as they pass through and out of the biprism 35 to make beams $D_1$ and $D_2$. Beams $D_1$ and $D_2$ are then incident on the phase grating 36. Phase grating 36 functions as a beam combiner and is constructed so that a portion of each incident beam, preferably 50%, passes through the grating unaffected and the remainder of each beam is diffracted. The diffraction angle is chosen so that the diffracted portion of each incident beam exits the grating colinearly with the transmitted or unaffected portion of the other incident beam. In this manner, the pass-through portion of beam $D_1$ and the diffracted portion of beam $D_2$ forms a mixed, or combined, light beam $M_1$. It will be appreciated by those skilled in the art that beam $M_1$ contains the interference product of beams $D_1$ and $D_2$. Similarly, the pass-through portion of beam $D_2$ and the diffracted portion of beam $D_1$ forms a mixed, or combined, light beam $M_2$. The light beams $M_1$ and $M_2$ may also be considered as comprising interfering portions of the reference beam $S_1$ and the signal beam $S_2$, since the relative phases of these beams do not change in the biprism 35. The light beams $D_1$ and $D_2$ comprise only light of the reference and signal beams $S_1$ and $S_2$, respectively, even when incident on the photodetector arrays 62.

The input coupling grating 32 is located generally at an input end 38 of the waveguide structure 12. As was described briefly above, the input coupling grating 32 is an integrated optic structure placed on or embedded in the planar waveguide 22 having a predetermined depth on or in the waveguide 22. The input coupling grating 32 performs the functions of redirecting the path of the incoming light, generally orthogonal to the waveguide 22, and stripping away unwanted modes so that a single mode propagates into the waveguide 22. The light source and input grating, possibly in combination with intermediate beam-shaping lenses (not shown), are effective to couple an optical beam measuring 100 µm to millimeters wide into the waveguide 22.

Alternate means for coupling the light beam into the planar waveguide 22, including prisms 27 or direct butt-coupling, could be used in place of the input coupling grating 32. As shown in FIG. 3B, a prism 27 is a triangular cross-section element constructed of a material having a higher refractive index than the waveguide 22. The prism 27 directs the light beam 15 into the waveguide 22 by refracting it at an angle dependent on the refractive index of the prism. As shown in FIG. 3C, butt-coupling is effected by placing the light source in direct contact with the input end 38 edge of the waveguide 22 or by focusing the light beam 15 through an intermediate transfer lens onto the input end 38 edge of the waveguide 22.

In the embodiment shown in FIGS. 1 and 3, the input coupling grating 32 is shown formed in the waveguide 22 adjacent the input end 38. The above-described fabrication techniques used to form the waveguide 22 may be used to form the coupling grating 32; other methods that are effective to cause periodic disturbances of the waveguide 22 or its refractive index, N, may also be used. As shown in FIG. 3, the grating is characterized by corrugations or periodic refractive index variations 40 having a period P of 0.2 to 1.5 µm, and a height H of 0.2 to 1.0 µm. The coupling efficiency of these types of integrated optics devices is typically in the range of 20–30%.

The light source 18 provides the light beam 15 to optically energize the sensor 10. The light source 18 can be a passive device such as an optical fiber pig tail 42 as is shown in the embodiment of FIG. 3. The optical fiber pig tail 42 is disposed in optical communication with the substrate lower surface 24, being held in place by epoxy 43. The pig tail 42 acts merely as a conduit for optical energy, thus it is a passive device. Alternatively, the light source 18 can be an active device such as a laser diode 44 shown in FIG. 3A. The laser diode 44 is energized by an external electric current through conduit 47 to generate the light beam 15 for energizing the sensor 10. The light source 18 in another embodiment could be an laser diode integrated into the body of the substrate 20 with electrical contacts in the form of wires extending from the sensor to be energized by external means or by electrical contacts printed onto the sensor which are caused to be disposed in electrical contact with mating contacts of an external power source. As would be obvious to those skilled in the art of sensor fabrication, the substrate 20 must be optically transparent to the frequency of light desired to energize the sensor 10 and have dispersive and other properties which do not inhibit the coupling of light into the planar waveguide 22. In yet another embodiment, the light source may be fabricated directly on the top surface of the waveguide 22, eliminating the need for an incoupling element. For purposes of this invention, integrating the light source 18 within the planar waveguide 22 or directly butt-coupling the light source 18 to the planar waveguide 22 are equivalent to the grating 32, prisms 27, lens, or other means for coupling a light beam 15 from a light source 18 into a planar waveguide 22 such that only one mode of the light beam 15 propagates in the planar waveguide 22.

Figure 1B:
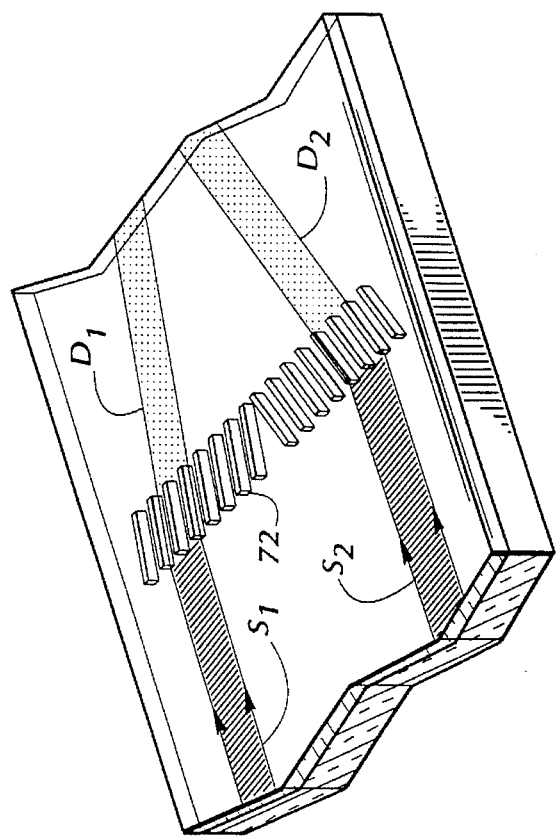
FIG. 1B is a partial perspective view of an embodiment of the interferometric sensor of the present invention, showing the use of an integrated optic diffraction grating in place of the integrated optic biprism of FIG. 1.
Figure 1A:
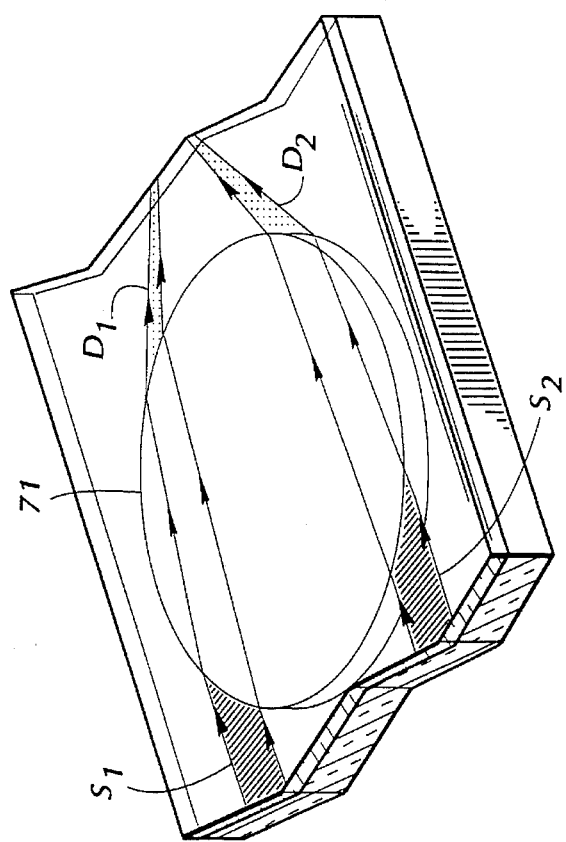
FIG. 1A is a partial perspective view of an embodiment of the interferometric sensor of the present invention, showing the use of a thin film lens in place of the integrated optic biprism of FIG. 1.

The integrated optic biprism 35 is located at a light output end 45 of the beam processing region 17. The biprism 35 is effective to receive the light beams passing from the beam processing region 17 and cause them to overlap at the phase grating 36 to be recombined thereat to produce an interfering beam. The biprism 35 is a thin film biprism functioning as a bulk prism to cause the reference and signal guided waves to deviate and overlap. The angular deviation of the beams, φ, is dependent on the refractive index difference between the prism region and the unaltered waveguide, and the apex angle of the prism, α. With effective mode index differences of 0.1 to 0.15, deviations of two to three degrees are achievable while retaining single mode operation. The biprism 35 is shown schematically in FIGS. 1 and 3. The biprism 35 includes an incident surface 46 through which the light beams, $S_1$ and $S_2$, pass. The prism also includes opposing surfaces 48 angularly disposed by the apex angle α. In a preferred embodiment, the apex angle α is in the range of 150–170 degrees and the adjacent angles are in the range of 5 to 15 degrees. These angular dimensions depend substantially on the structural dimensions of the sensor and may of course fall outside the ranges cited herein as required to accommodate those dimensions. Alternative integrated optic structures may serve as a means for deflecting the light beams and be used in lieu of biprism 35, including an integrated optic lens 71, shown in FIG. 1A, or an integrated diffraction grating 72, shown in FIG. 1B.

In FIG. 1, the phase grating 36 serves as a beam combiner for the deflected reference and signal beams $D_1$ and $D_2$. This type of grating provides easily controlled diffraction efficiency and is easily generated by photolithographic techniques, since the grating period G is typically in the range of 1 to 5 μm. The grating period G is dependent on the deviation angle φ produced by the biprism, the wavelength of the guided light λ, and the effective mode index $N_{eff}$ of the waveguide and is calculated by the following expression:

$$2N_{eff} G \cdot \sin\Theta = M\lambda,$$

where Θ is the Bragg angle of the phase grating and M=1. As can be seen from FIG. 1, in order for one deflected beam to combine with the portion of the other deflected beam that is diffracted by the phase grating, the prism deflection angle φ should be the same as the Bragg angle Θ.

To keep the overall length of the sensor equal to 50 mm or less using a 2 mm wide beam, the prism deflection angle φ should be approximately 2.8 degrees. Thus the Bragg angle Θ of the phase grating will also be 2.8 degrees. At an operating wavelength of 0.780 μm this corresponds to a grating period G of 5.2 μm assuming an effective waveguide mode index of refraction of 1.52. In terms of photolithographic capabilities utilized in the fabrication of the integrated optics, these are relatively large dimensions and are easily reproduced.

In practice a single photolithographic mask can be used to fabricate both the biprism 35 and the phase grating 36 simultaneously. The grating can be fabricated as a surface relief structure or as an embedded grating. Also, because the grating period is coarse, the angular selectivity of the grating is quite large implying alignment of the guided wave and the grating is straightforward. Note that, as discussed above, either an integrated optic lens, an integrated optic diffraction grating, or a total internal reflection element could be used in place of the biprism.

Figure 1D:
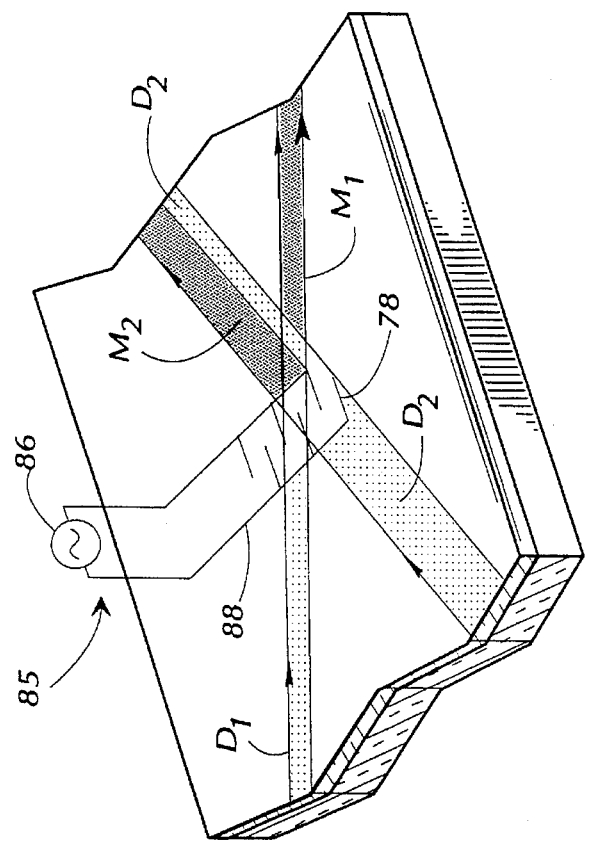
FIG. 1D is a partial perspective view of an embodiment of the interferometric sensor of the present invention, showing the use of an electro-optic device in place of the phase grating of FIG. 1.
Figure 1C:
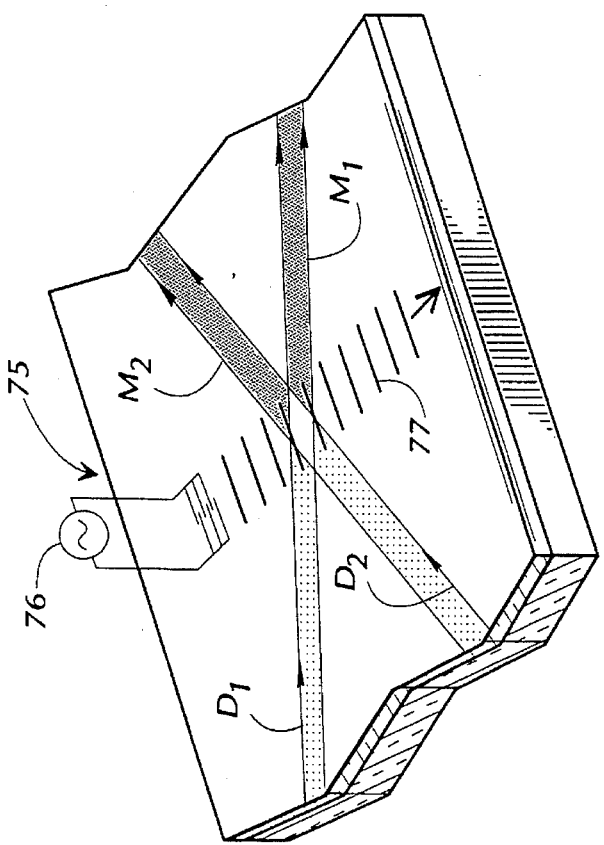
FIG. 1C is a partial perspective view of an embodiment of the interferometric sensor of the present invention, showing the use of an acousto-optic device in place of the phase grating of FIG. 1.

It is also informative to note that while the phase grating 36 offers a passive, fully integrated means for effecting beam combination, other means for producing an output beam indicative of beam-portion combinations are available and applicable. For example, an acousto-optic device 75, shown in FIG. 1C, may be used to vary the index of refraction of the waveguide so as to cause beam combination. The acousto-optic device 75 is a planar waveguide 22 constructed with an acousto-optic material. Applying a control voltage 76 to the acousto-optic material establishes a phase grating in the waveguide. The advantage of the acousto-optic device 75 is that the control voltage 76 can be varied, resulting in a varying phase grating 77 propagating across the waveguide. Alternatively, an electro-optic device 85 may be constructed by applying a piezoelectric layer with conventional methods to the waveguide, as shown in FIG. 1D. Interdigital transducers 88 may deposited on one surface of the waveguide 22 and connected to a control voltage 86. Varying the control voltage 86 will emulate the phase grating so as to effect beam combination.

Figure 2:
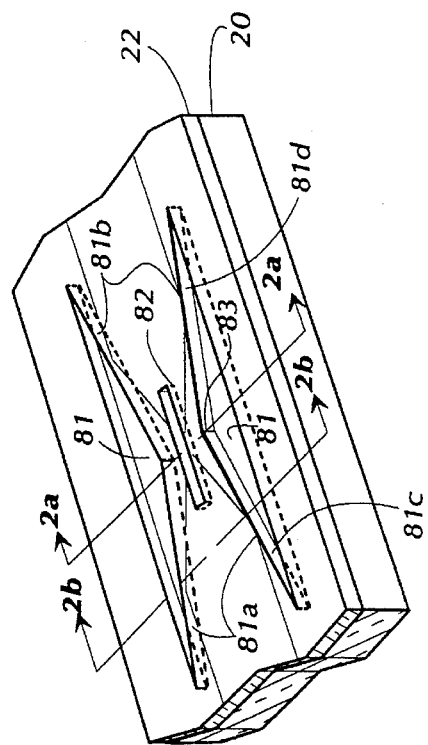
FIG. 2 is a partial perspective view of an embodiment of the interferometric sensor of the present invention, showing the use of total internal reflection elements and a Fresnel reflection element in place of the integrated optic biprism and phase grating of FIG. 1.
Figure 2A:
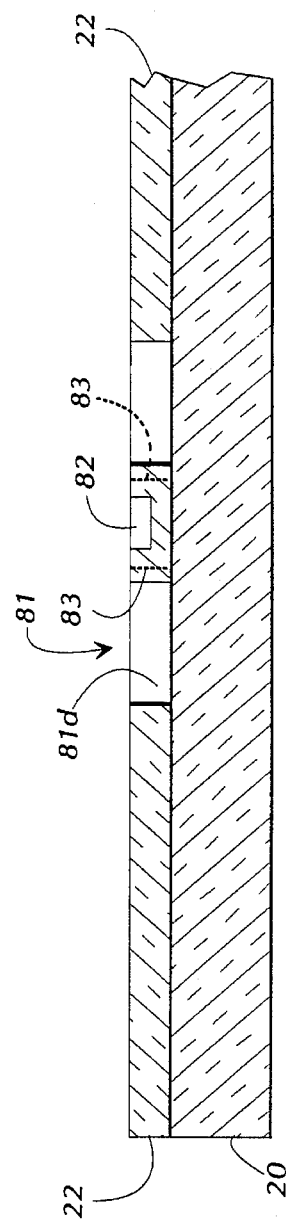
FIG. 2A is a cross-sectional view of the embodiment shown in FIG. 2, taken along lines $2a$—$2a$ of FIG. 2, showing a sectional view of the integrated optic elements of the interferometric sensor.
Figure 2B:
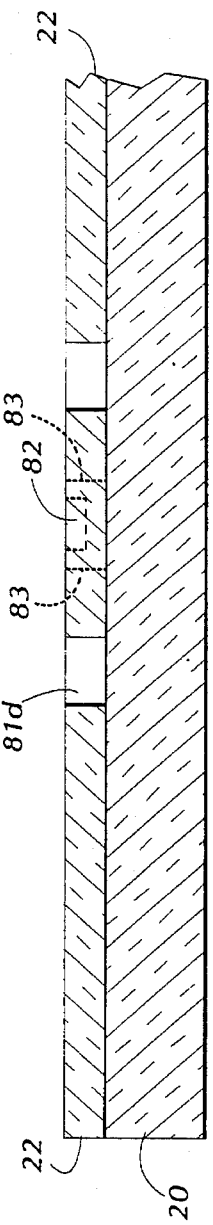
FIG. 2B is a cross-sectional view of the embodiment shown in FIG. 2, taken along lines $2b$—$2b$ of FIG. 2, showing a sectional view of the integrated optic elements of the interferometric sensor.

As shown in FIG. 2, the integrated optic biprism 35 and phase grating 36 combination could be replaced by a total internal reflection element 81 and Fresnel reflection element 82 combination. The total internal reflection elements 81 are created by wedge-shaped voids in the waveguide 22. The reflection elements 81 have internal faces 81a and 81b and external faces 81c and 81d. The angle formed by the external faces 81c and 81d at the apex 83 of a wedge-shaped void is large enough so that the guided waves in the wave guide are totally reflected from internal faces 81a and impinge on a Fresnel reflection element 82. The Fresnel reflection element 82 consists of narrow strips of thinner and thicker waveguide regions, shown in cross-section in FIG. 2B. The Fresnel reflection element 82 is used to reflect and transmit portions of the guided waves and effect beam combination of the reflected and transmitted portions. The combined beam then reflects from internal faces 81b toward the light detector for the sensor.

The beam processing region 17 includes a reference region 52 and a signal region 54. The regions 52 and 54 may be defined by and may exist because of the deposition of one or more layers of selective overlays 55 and/or one or more layers of protective overlays 60 on the upper surface of the waveguide 22 at a contact interface 56 in a generally elongated rectangular patch as shown in FIG. 1. The reference region and sensing region may also be defined by varying the material used to construct the waveguides. Geometric shapes other than the rectangles shown in FIG. 1 may be used when appropriate to the application of the sensor. Furthermore, the reference region 52, the signal region 54, or both may be subdivided into several subregions by defining multiple selective overlays on the waveguide surface. Whatever the shapes selected, the beam processing region 17 should be designed so that the reference beam $S_1$ is comprised primarily of light passing through the reference region 52 and the signal beam $S_2$ is comprised primarily of light passing through the signal region 54. It should be noted that FIGS. 8A–8C are not drawn to scale; the thickness of the overlays 55 and 60 have been exaggerated for illustration purposes. Typical thicknesses of selective overlays 55 range from a single atomic layer to a fraction of a millimeter.

The selective overlays 55 are disposed in optical contact with the waveguide along the contact interface 56 and affect the propagation of light through one of the regions 52 or 54 relative to the propagation of light through the other region. The selective overlays 55 act either to cause a change of the propagation of light through the regions or to prevent a change in the propagation of light through a region. As was explained briefly above, the difference in propagation of the light through the regions provides the mechanism by which the sensor functions. The light beams, $S_1$ and $S_2$, each slightly different from the other, are later combined in the phase grating 36 which produces the light beams $M_1$ and $M_2$ which are interfering beams, the interpretation of which provides information about the environment measured.

Selective overlays 55 may have refractive indices lower than the waveguide 22 or they may have refractive indices higher than the waveguide if the selective overlay 55 is sufficiently thin relative to the waveguide thickness, or they may also have refractive indices that are variable when exposed to the environment to be measured. For example, a localized chemical interaction, such as covalent bonding, hydrogen bonding absorption or adsorption among others, between a chemical component of the environment and a chemo-responsive selective overlay 55 may cause the refractive index to change in proportion to the concentration or strength of the environmental component. The change in refractive index affects the propagation of light through the region covered by the selective overlay. Chemical binding between the environmental substance under test and the chemo-responsive selective overlay 55 may also cause changes in the overall configuration (usually the thickness) of the selective overlay which will affect propagation of light through the region covered by the selective overlay. The magnitude of the variation of the propagation of light through the region can be correlated with the concentration of environmental components or other characteristic of the environment. In a preferred embodiment for a gaseous ammonia sensor, the selective overlay may be a thin film of polyvinyl alcohol, with a proton exchange between the ammonia gas and the polyvinyl alcohol film causing the refractive index of the polyvinyl alcohol film to change in proportion to the concentration of the ammonia present.

As shown in FIG. 8A, the environment itself can act as an selective overlay for sensing a physical property of an environment. In that case the signal region 54 is defined by a portion of the waveguide which does not receive a selective material coating. The reference region 52 is coated with the protective overlay 60 so as to be unaffected or affected differentially by exposure to the environment. Here, an interaction occurs between the waveguide upper surface 28 and the environment directly. A humidity sensor responsive to relative humidity is an example where environmental moisture interacts, interstitially, with the waveguide upper surface 28 which causes a localized change in the signal region 54 refractive index.

A particular example, shown in FIG. 8B, of a chemoresponsive layer for use with the sensor 10 is one in which the selective overlay 55 is a layer of biomolecules caused to be adhered to the waveguide surface, where the biomolecules are one member of a molecular binding pair. Antigens, antibodies, enzymes, lectins or single-stranded nucleic acids, for instance, could be bound to the signal region 54 of the waveguide surface. In this case the signal region 54 is said to be functionalized to bring about specific molecular binding. When a solution containing the other member of the binding pair is exposed to the sensor, specific molecular binding between the binding pair changes the refractive index of the waveguide in the signal region 54. As a result, the phase of the signal beams is altered, and combining the signal beam $S_2$ with the reference beam $S_1$ provides information regarding the presence of the second member of the binding pair. In a preferred embodiment for detection of influenza A virus, the selective overlay may be a layer of monoclonal antibodies specific to the NP proteins of influenza A.

Because the selective overlay 55 itself may have a spontaneous effect on the refractive index of the waveguide, and on the propagation of light therethrough even without exposing the sensor to the environment, it may become necessary to normalize the waveguide. This is done, as shown in FIG. 8C, by adding a layer of the particular selective overlay 55 to the reference region 52, then covering the selective overlay 55 disposed on the reference region 52 with a protective overlay 60. The protective overlay 60 forms an optically insensitive layer so that when the sensor is exposed to the environment the environment has no effect on the refractive index of the selective overlay 55 defining the reference region 52 nor on the propagation of light through the reference region 52. Protective overlays may be fabricated, for example, from silicon dioxide or polytetrafluoroethylene.

In another embodiment the sensor 10 may be adapted to measure electric fields in the environment by providing a selective overlay 55 whose refractive index changes in response to applied electric fields or by constructing the planar waveguide 22 or substrate 20 from a material that is responsive to applied electric fields. Similarly, the sensor is adapted to measure magnetic conditions or mechanical forces in the environment by providing a selective overlay 55 of, or by constructing the planar waveguide 22 or substrate 20 from, a material whose refractive indices change in response to exposure to a magnetic field or mechanical forces, respectively. Materials with a refractive index that changes in response to applied electric fields include, for example, polyvinylidene or lithium niobate. Materials with a refractive index that changes in response to a magnetic field include, for example, nickel-polymer structures. Materials with a refractive index that changes in response to a mechanical force include, for example, polymers such as polystyrene or methylmethacrylate.

As light is injected into the planar waveguide 22 by the input coupling grating 32 and propagates through the regions 52 and 54, the selective material applied to the signal region 54 is seen by the evanescent field of the signal beam $S_2$ and as a result the phase of the signal beam $S_2$ is altered. When combined (after deflection) with the unaltered or differentially altered reference beam $S_1$ by the phase grating 36, the resulting phase shift manifests itself as sinusoidal intensity variations in both output beams $M_1$ and $M_2$ due to interference effects. The intensities of the output beams $M_1$ and $M_2$ are described by the following output beam intensity equations:

$$I_{m_1} = I_{s_1} + I_{s_2} + 2[I_{s_1} \cdot I_{s_2}]^{1/2} [\cos(\Phi_0 + \Delta\Phi)] \text{ and}$$

$$I_{m_2} = I_{s_1} + I_{s_2} + 2[I_{s_1} \cdot I_{s_2}]^{1/2} [\cos(\Phi_0 + \Delta\Phi + \pi)],$$

where $I_{m_1}$ = intensity of output beam $M_1$ $I_{m_2}$ = intensity of output beam $M_2$ $I_{s_1}$ = intensity of reference beam $S_1$ $I_{s_2}$ = intensity of signal beam $S_2$ $\Phi_0$ = constant phase bias resulting from the waveguide structure construction parameters $\Delta N_{eff} = N_{eff(s_1)} - N_{eff(s_2)}$ $N_{eff(s_1)}$ = effective index of refraction of the waveguide structure reference region 52

$N_{eff(s_2)}$ = effective index of refraction of the waveguide structure signal region 54

L = physical length of beam processing region 17, and

λ = free space wavelength of the light beams.

These equations show that the magnitude of the change in output beam intensities $I_{m_1}$ and $I_{m_2}$ is a function of the length, L, of the beam processing region 17 times the difference in the effective indices of refraction of regions 52 and 54. Thus, for a change in an environmental condition which changes the index of refraction of the signal region 54, the sensitivity of the sensor 10 is in direct proportion to the length, L.

The integrated optic light block 34 assists to define more discretely the waveguide regions 52 and 54 by blocking light that propagates within a prescribed area along the center of the waveguide, parallel to the regions 52 and 54 along the opposing inner edges of the regions 52 and 54. The light block 34 is constructed of an opaque or light-absorbing material and prevents light which is neither of the character of the signal region 54 nor of the reference region 52 from commingling with the light of light beams $S_1$ and $S_2$, thereby reducing the sensor sensitivity.

As previously described, the beams $S_1$ and $S_2$ pass through the biprism 35 and are refracted, which for the preferred embodiment is typically at an angle 2 to 3 degrees, causing the beams to overlap at the phase grating 36 at which point portions of the beams are combined. While the beams $M_1$ and $M_2$ provide information specific about the change in refractive index and of the environment, the beams $D_1$ and $D_2$ are useful for indicating operating variation of the sensor due to, for example, fluctuations in the power input or thermally induced changes in the output. Therefore, beams $D_1$ and $D_2$ can be used to normalize beams $M_1$ and $M_2$ and thereby remove any spurious effects caused by power fluctuations or thermal changes.

Figure 1E:
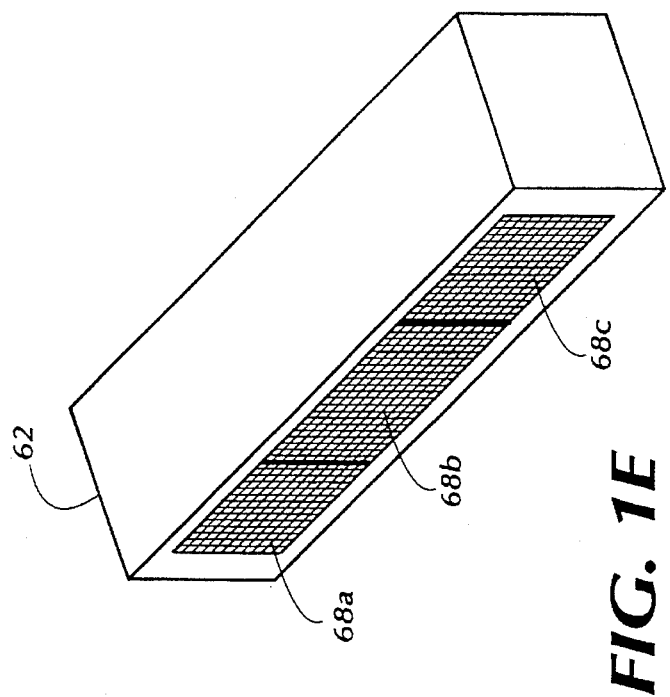
FIG. 1E is an perspective view of a light detector for use with the present invention, showing the portions of the photodetectors arrays which receive light beams $D_1$, $M_1$, and $S_2$, respectively.

The light detector for the sensor may include photodetector arrays 62 which are disposed along portions of an edge 64 of the waveguide structure 12. Each photodetector array 62 defines a light receiving face 66 facing the waveguide structure 12 such that light sensing elements 68 mounted to each face 66 are disposed in optical communication with the output beams. As shown in FIG. 1 and in more detail in FIG. 1E, the light sensing elements 68 of the photodetector arrays 62 are adapted to receive the light beam outputs, with one portion 68a of one array receiving light beam $D_1$, a second portion 68b of the same array receiving light beam $M_1$, and a third portion 68c of the same array receiving light beam $S_2$, while light beams $D_2$, $M_2$, and $S_1$ are received by the light sensing elements 68 of the other array. The light sensing elements 68 may, for example, comprise a charge coupled device (CCD) or multiple discrete PIN diodes.

Alternate means for coupling the output beam 16 to the photodetector arrays 62, other than mounting the arrays along the output edge 64 of the waveguide structure 12 are available. The photodetector arrays 62 can be coupled to the output beam 16 by means of output coupling gratings 33, prisms 37, or total internal reflection mirrors 50. As shown in FIG. 3D, the output coupling grating 33 is an integrated optic structure embedded in or placed on the planar waveguide 22 similar to the input coupling grating 32 described above. The output coupling grating 33 directs the output beams 16 out of the waveguide 22 through the substrate 20 and out of the substrate lower surface 24 at an angle dependent on the period of the grating and the wavelength of the light source. As shown in FIG. 3E, the prism 37 is a triangular cross-section element constructed of a material having a higher refractive index than the waveguide 22. The prism 37 directs the output beams 16 out of the waveguide 22 at an angle dependent on the refractive index of the prism. As shown in FIG. 3F, the total internal reflection mirror 50 can be constructed by introducing a polished bevel 39 into the output edge 64 of the waveguide 22. The total internal reflection mirror 50 directs the output beams 16 out of the waveguide 22 through the substrate 20 and out of the substrate lower surface 24 at an angle dependent on the angle of the bevel. As shown in FIG. 3F, a preferred angle is 45 degrees. Another means for coupling the output beams 16 to the photodetector arrays 62 is to integrate the light sensing elements 68 within the waveguide 22. Such integration may be accomplished either with hybrid techniques (mounting the elements flush to the waveguide, for example) or by monolithic techniques (i.e., creating the detector simultaneously with the waveguide).

As previously described the intensities of the output beams $M_1$ and $M_2$, graphically displayed in FIGS. 4A and 4B, vary sinusodially as the difference between the effective refractive indexes of the regions 52 and 54 varies linearly. Changes in the sinusoidal patterns of the intensities of the output beams $M_1$ and $M_2$ can be correlated to the environmental condition being measured. The output of beam $M_1$ is 180 degrees out of phase with the output beam $M_2$ due to conservation of energy. The most valuable and least ambiguous information is provided by a sinusoidal display at the point of greatest slope or the point of quadrature. To ensure that the intensity of one of the output beams $M_1$ and $M_2$ is always around the point of quadrature it is preferred to have the output be at $M_1$ 90 degrees out of phase with the output beam $M_2$. This may be accomplished by adopting a ¼ wave filter between the waveguide structure 12 and one of the photodetector arrays 62 or by incorporating as an integrated optic component in the waveguide, a phase grating structure for example, along the path of one of the beams $M_1$ or $M_2$.

Figure 5:
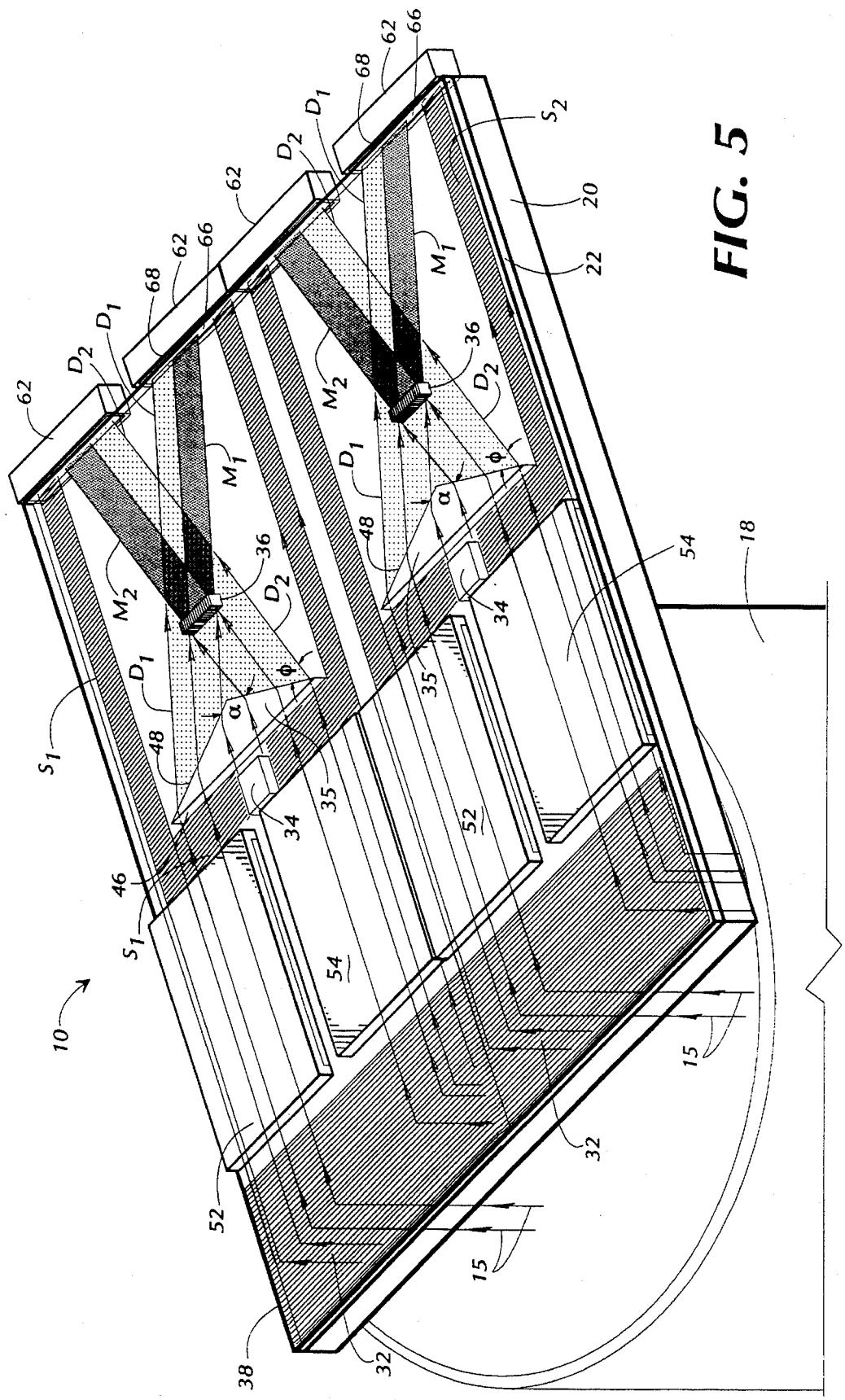
FIG. 5 is a perspective view of an integrated multi-sensor embodiment of the present invention having two interferometric sensors mounted on a single substrate.
Figure 6:
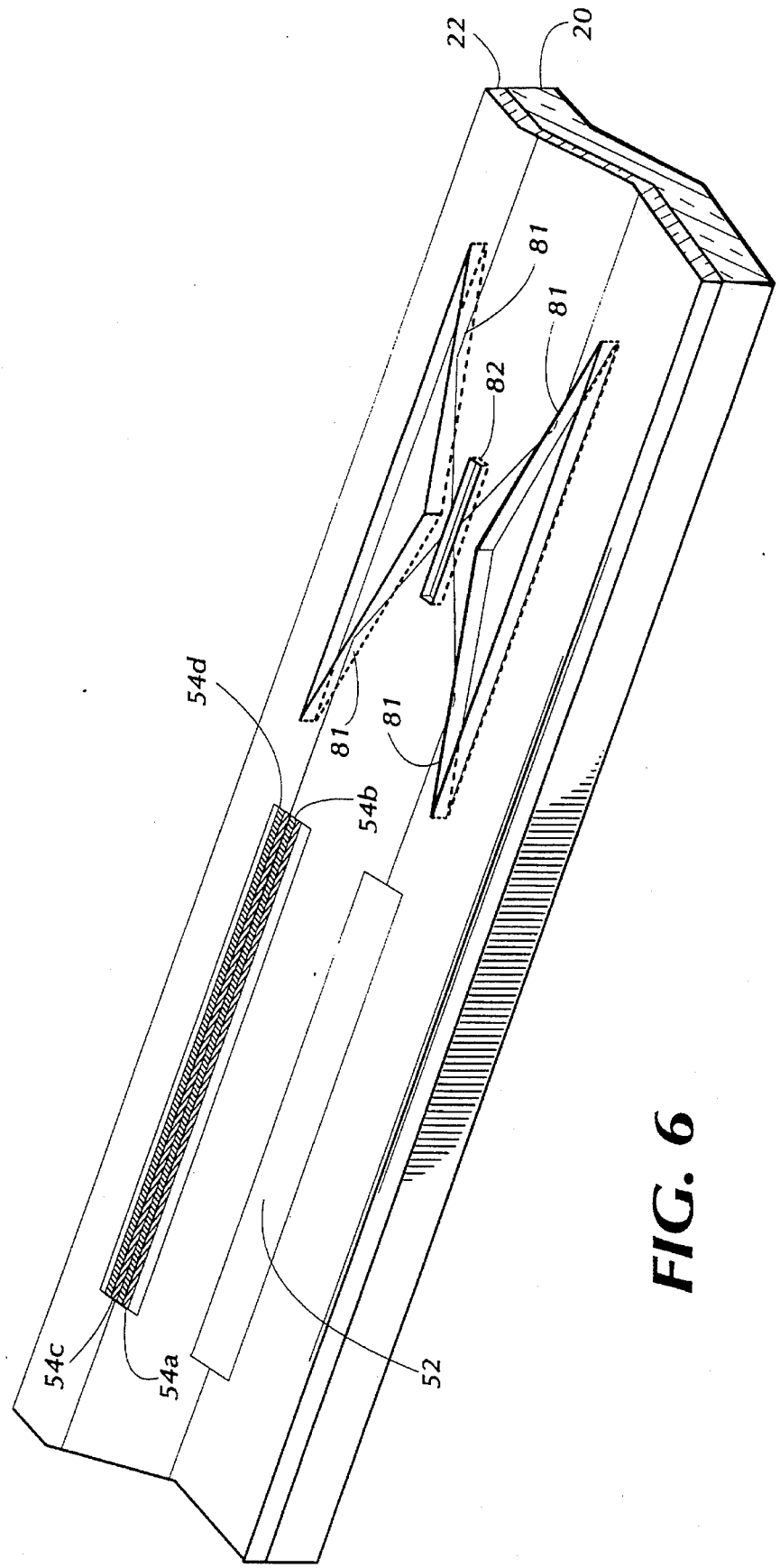
FIG. 6 is a partial perspective view of the embodiment shown in FIG. 2, illustrating subdividing the signal arm to produce multiple sensing subregions for multiple species sensing or enhanced signal processing.

The beam processing region 17 can also be divided into more than one reference region 52 and/or more than one signal region 54. For example, the embodiment depicted in FIG. 5 shows two reference regions 52 paired with two signal regions 54. Alternatively, FIG. 6 depicts multiple signal regions 54a, 54b, 54c, 54d, all sharing the same reference region 52. The analysis set forth above applies to each reference and signal region pair. However, the advantage of multiple reference and/or sensing regions in the same sensor 10 is that the construction parameters, such as the materials (preferably chosen for the material characteristics such as optical properties or chemical properties) used or the configuration (e.g., shape and size) employed for the waveguide structure 12 can be different for each pair. This allows additional differential information to be detected by the photodetector arrays 62 and permits sensing of multiple environmental effects and/or enhanced signal processing.

An example of enhanced signal processing is to construct each of the two reference regions 52 and signal regions 54 in FIG. 5 to be essentially the same physical length and to treat each of the signal regions with the same environmentally-sensitive selective overlay 55. With appropriate choices for the configurations and/or the materials of the waveguide 22 or substrate 20 underlying each of the reference regions 52 and signal regions 54, one skilled in the art can cause each of the two reference-signal pairs to have a different constant phase bias $\Phi_0$ and a negligible sensitivity difference. The different constant phase biases mean that the otherwise essentially identical output generated by each reference-signal pair will image a different portion of its sinusodially varying output interference pattern on its photodetector arrays 62. By constructing one constant phase bias to be $\pi/2$ radians (90 degrees) different from the other, it can be insured that at all times at least one of the outputs is being imaged near the quadrature, or highest sensitivity, portion of the interference pattern, thereby eliminating relatively insensitive output regions.

Another example of enhanced signal processing is shown in FIGS. 7A and 7B. FIGS. 7A and 7B depicts total internal reflection elements 81 and a Fresnel reflection element 82, shown in further detail in FIG. 2. As shown in FIGS. 7A and 7B, the construction of the environmentally-sensitive selective overlay 55 on the signal regions of reference-signal pairs $I_1$ ($I_{1r}$ and $I_{1s}$) and $I_2$ ($I_{2r}$ and $I_{2s}$) is longer than the otherwise essentially identical environmentally-sensitive selective overlay 55 on the signal region of reference-signal pair $I_3$ ($I_{3r}$ and $I_{3s}$). As given by the output beam intensity equations set forth above, and as shown in the output interference patterns for each reference-signal pair ($I_{1rs}$, $I_{1sr}$, $I_{2rs}$, etc.), the longer selective overlay 55 multiplies the sensing effect in proportion to the length of the overlay. In particular, it is seen that varying the length of the overlay varies the slope of the output interference pattern at quadrature. This slope is the phase change of the interferometer (at quadrature) per unit change in the environmental effect being measured, commonly called the sensitivity of the interferometer. The longer length reference-signal pairs $I_1$ and $I_2$ provide high resolution information, and the shorter length reference-signal pair $I_3$ provides low resolution information concerning the same environmental effect. In the embodiment shown in FIGS. 7A and 7B, the 90 degree constant phase bias difference between the high resolution signal pairs $I_1$ ($I_{1r}$ and $I_{1s}$) and $I_2$ ($I_{2r}$ and $I_{2s}$) is caused by appropriate differences in the configurations or materials of the planar waveguide 22 or substrate 20 underlying those sensing regions, as previously described, and insures that at all times the outputs from at least one of these two signal pairs is near quadrature. Similarly, by appropriate choices for the construction parameters for the waveguide structure 12, the constant phase bias difference between signal pair $I_3$ and $I_1$ can be minimized. Reference-signal pair $I_4$ ($I_{4r}$ and $I_{4s}$), not subject to any overlays, provides control information.

It is noted that the above signal processing techniques are applicable to any sensor propagating electromagnetic waves in a planar construct. Furthermore, they are applicable regardless of the number or type of modes propagating in the planar construct. They are particularly useful in integrated optic planar constructs. Thus, the enhanced signal processing techniques disclosed here provide improvements to planar constructs having channel waveguides such as Mach-Zehnder interferometric sensors (i.e., U.S. Pat. No. 4,515,430) as well as planar constructs having planar waveguides such as the interferometric sensors disclosed in detail above or in U.S. Pat. No. 4,940,328 or U.S. Pat. No. 5,120,131.

It is to be understood that the above-described embodiments are simply illustrative of the invention. While this invention has been described in detail with particular reference to preferred embodiments thereof, it will be understood that variations and modifications can be made to these embodiments without departing from the spirit and scope of the invention as described herein and as defined in the appended claims.

I claim:

1. An apparatus for detecting a property of an environment, comprising:
   a. means for producing a beam of coherent radiation;
   b. a planar waveguide, comprising:
      i. a first region that allows radiation to propagate therethrough as a first function of exposure to the property of the environment; and
      ii. a second region, distinct from the first region, that allows radiation to propagate therethrough as a second function of exposure to the property of the environment, the second function being different from the first function;
   c. means for coupling the beam into the planar waveguide; and
   d. means for determining a phase difference between a first part of the beam after having propagated through the first region and a second part of the beam after having propagated through the second region, the apparatus having a structural feature that restricts transmission of the beam through the planar waveguide to only a single mode of the beam.

2. The apparatus of claim 1, wherein the coupling means comprises a coupling grating for directing the beam of radiation from the source into the planar waveguide.

3. The apparatus of claim 1, further comprising means for indicating to a user a comparison of the phase difference to a predetermined phase difference corresponding to the property of the environment.

4. The apparatus of claim 1, wherein the first region comprises a material having an index of refraction that varies in response to a variance of the property of the environment.

5. The apparatus of claim 1, wherein the first region comprises a material that interacts with the property of the environment so that the index of refraction of the first region varies in response to a variance of the property of the environment.

6. The apparatus of claim 1, wherein the first region comprises a material that has a configuration that varies in response to a variance of the property of the environment.

7. The apparatus of claim 1, wherein the first region has an exterior surface and wherein a material that affects propagation of the beam through the first region is disposed adjacent to at least a portion of the exterior surface.

8. The apparatus of claim 7, wherein the material has an index of refraction that varies in response to a variance of the property of the environment.

9. The apparatus of claim 7, wherein the material interacts with the property of the environment so that the index of refraction of the first region varies in response to a variance of the property of the environment.

10. The apparatus of claim 7, wherein the material has a configuration that varies in response to a variance of the property of the environment.

11. The apparatus of claim 7, wherein the material comprises a dopant layer grown on the planar waveguide.

12. The apparatus of claim 7, wherein the material comprises a dopant layer implanted in the planar waveguide.

13. The apparatus of claim 7, wherein the material comprises a layer applied to the planar waveguide.

14. The apparatus of claim 1, further comprising a substrate in contact with the planar waveguide that provides support for the planar waveguide and that affects propagation of the beam through the first region.

15. The apparatus of claim 14, wherein at least a portion of the substrate comprises at least one material having a refractive index that varies in response to a variance of the property of the environment.

16. The apparatus of claim 14, wherein at least a portion of the substrate comprises at least one material that interacts with the property of the environment so that the index of refraction of the first region varies in response to a variance of the property of the environment.

17. The apparatus of claim 14, wherein at least a portion of the substrate comprises at least one material having a configuration that varies in response to a variance of the property of the environment.

18. The apparatus of claim 1, wherein the phase difference determining means comprises:
   a. means for combining a portion of the first part of the beam with a portion of the second part of the beam, thereby creating an interference product beam; and
   b. means for detecting the interference product beam.

19. The apparatus of claim 18, wherein the combining means comprises:
   a. means for deflecting a portion of the first part of the beam and a portion of the second part of the beam so that the portion of the first part of the beam intersects the portion of the second part of the beam at a point of intersection; and
   b. means, disposed at the point of intersection, for producing at least one output beam indicative of at least one combination of the first part of the beam and the second part of the beam.

20. The apparatus of claim 18, wherein the detecting means comprises:
   a. an array of photodetectors; and
   b. an output grating coupler for directing a portion of the interference product beam to the array of photodetectors.

21. The apparatus of claim 1, wherein the structural feature comprises the transverse dimension of the planar waveguide.

22. The apparatus of claim 1, wherein the structural feature comprises the index of refraction of the planar waveguide.

23. The apparatus of claim 1, wherein the structural feature comprises the index of refraction and the transverse dimension of the planar waveguide.

24. The apparatus of claim 1, wherein the structural feature comprises the geometry of the coupling means.

25. An apparatus for detecting a concentration of a substance, comprising:
   a. means for producing a beam of coherent radiation;
   b. a planar waveguide having an exterior surface and being capable of transmitting only one mode of the beam, comprising:
      i. a first region, having an exterior surface, that allows radiation to propagate therethrough;
      ii. a second region that allows radiation to propagate therethrough; and
      iii. a material, disposed adjacent the exterior surface of the first region, that has a first index of refraction when the material is exposed to the concentration of the substance and a different index of refraction when the material is not exposed to the concentration of the substance;
   c. means for coupling the beam into the planar waveguide;
   d. means for determining a phase difference between the first part of the beam after having propagated through the first region and the second part of the beam after having propagated through the second region;
   e. means for comparing the phase difference to a predetermined phase difference associated with the concentration of the substance; and
   f. means for indicating to a user when the phase difference corresponds to a predetermined phase difference that indicates the concentration of the substance.

26. A method of detecting a concentration of a substance, comprising the steps of:
   a. producing a beam of coherent radiation;
   b. coupling the beam into a planar waveguide that has an exterior surface so that only one mode of the beam is transmitted, so that a first part of the beam propagates through a first region and so that a second part of the beam propagates through a second region, the step further comprising:
      i. adapting the first region so that the first region allows the radiation to propagate therethrough as a first function of exposure to the substance; and
      ii. adapting the second region so that the second region allows the radiation to propagate therethrough as a second function of exposure to the substance, the second function being different from the first function;
   c. determining a phase difference between the first part of the beam after having propagated through the first region and the second part of the beam after having propagated through the second region;
   d. generating a signal indicative of the phase difference;
   e. comparing the phase difference signal to a predetermined signal that corresponds to a phase difference expected when the first region is exposed to the concentration of the substance; and
   f. indicating to a user when the phase difference signal corresponds to the predetermined signal, thereby indicating that the first region is exposed to the concentration of the substance.

27. Am apparatus for sensing a property of the environment to which the apparatus is exposed, comprising:
   a. means for generating a beam of coherent radiation;
   b. a planar construct;
   c. means for coupling the beam into the planar construct;
   d. at least one reference region in the planar construct;
   e. a plurality of signal regions in the planar construct, wherein each of the signal regions is paired with at least one reference region;
   f. a plurality of beam combiners for pairwise combining of light beam portions emanating from at least one of the reference regions with light beam portions emanating from the signal regions, thereby creating a plurality of output beams, at least one of the output beams being associated with each reference/signal region pair; and
   g. means for determining an intensity of at least one of the output beams.

28. The apparatus of claim 27, wherein at least one construction parameter of the sensor is different for at least one of the plurality of pairs of reference/signal regions, thereby causing a constant phase bias difference between at least two of the output beams.

29. The apparatus of claim 28, wherein the constant phase bias difference is approximately ninety degrees.

30. The apparatus of claim 28, wherein the construction parameters are chosen from the group consisting of planar construct configuration and planar construct materials.

31. The apparatus of claim 27, wherein at least one construction parameter of the sensor is different for at least one of the plurality of pairs of reference/signal regions, thereby causing the output interference pattern of an output beam associated with the one of the plurality of pairs of reference/signal regions to have a different slope at quadrature compared to the output interference pattern of at least one other of the output beams.

32. The apparatus of claim 31, wherein the construction parameters are chosen from the group consisting of planar construct configuration and planar construct materials.

33. The apparatus of claim 27, further comprising an overlay over the planar construct.

34. The apparatus of claim 33, wherein at least one construction parameter of the sensor is different for at least one of the plurality of pairs of reference/signal regions, thereby causing a constant phase bias difference between at least two of the output beams.

35. The apparatus of claim 34, wherein the constant phase bias difference is approximately ninety degrees.

36. The apparatus of claim 34, wherein the construction parameters are chosen from the group consisting of planar construct configuration, planar construct materials, overlay configuration, and overlay materials.

37. The apparatus of claim 33, wherein at least one construction parameter of the sensor is different for at least one of the plurality of pairs of reference/signal regions, thereby causing the output interference pattern of an output beam associated with the one of the plurality of pairs of reference/signal regions to have a different slope at quadrature compared to the output interference pattern of at least one other of the output beams.

38. The apparatus of claim 37, wherein the construction parameters are chosen from the group consisting of planar construct configuration, planar construct materials, overlay configuration, and overlay materials.

39. The apparatus of claim 27, further comprising a substrate in contact with the planar construct.

40. The apparatus of claim 39, wherein at least one construction parameter of the sensor is different for at least one of the plurality of pairs of reference/signal regions, thereby causing a constant phase bias difference between at least two of the output beams.

41. The apparatus of claim 40, wherein the constant phase bias difference is approximately ninety degrees.

42. The apparatus of claim 40, wherein the construction parameters are chosen from the group consisting of planar construct configuration, planar construct materials, substrate configuration, and substrate materials.

43. The apparatus of claim 39, wherein at least one construction parameter of the sensor is different for at least one of the plurality of pairs of reference/signal regions, thereby causing the output interference pattern of an output beam associated with the one of the plurality of pairs of reference/signal regions to have a different slope at quadrature compared to the output interference pattern of at least one other of the output beams.

44. The apparatus of claim 43, wherein the construction parameters are chosen from the group consisting of planar construct configuration, planar construct materials, substrate configuration, and substrate materials.

* * * * *